United States Patent
Steinbacher (10) Patent No.: US 8,038,619 B2
(45) Date of Patent: Oct. 18, 2011

(54) MOTOR DRIVER FOR ULTRASOUND SYSTEM

(75) Inventor: Franz Steinbacher, Voecklamarkt (AT)

(73) Assignee: General Electric Company, Schenectady, NY (US)

(*) Notice: Subject to any disclaimer, the term of this patent is extended or adjusted under 35 U.S.C. 154(b) by 738 days.

(21) Appl. No.: 12/112,911

(22) Filed: Apr. 30, 2008

(65) Prior Publication Data

US 2009/0012401 A1    Jan. 8, 2009

Related U.S. Application Data (60) Provisional application No. 60/914,893, filed on Apr. 30, 2007.

(51) Int. Cl.
*A61B 8/00* (2006.01)
*A61B 8/14* (2006.01)
*G05F 1/00* (2006.01)

(52) U.S. Cl. .......... 600/444; 600/459; 318/678
(58) Field of Classification Search .......... 600/437, 600/441, 444, 459; 128/916
See application file for complete search history.

(56) References Cited

U.S. PATENT DOCUMENTS 5,159,931 A * 11/1992 Pini .............................. 600/443
7,282,878 B1 * 10/2007 Rakov et al. .............. 318/400.01
7,534,211 B2 * 5/2009 Hwang et al. ................. 600/459

* cited by examiner

*Primary Examiner* — Michael T Rozanski
(74) *Attorney, Agent, or Firm* — Dean Small; The Small Patent Law Group (57) ABSTRACT

A motor driver for an ultrasound system is provided. The ultrasound system includes a transmitter and receiver, both communicatively coupled to a transducer array of an ultrasound probe. The ultrasound system further includes a digital motor driver for controlling movement of the transducer array.

24 Claims, 10 Drawing Sheets

MOTOR DRIVER FOR ULTRASOUND SYSTEM

CROSS-REFERENCE TO RELATED APPLICATIONS

This application claims priority to and the benefit of the filing date of U.S. Provisional Application No. 60/914,893 filed, Apr. 30, 2007 for "PORTABLE 3D/4D ULTRASOUND," which is hereby incorporated by reference in its entirety.

BACKGROUND OF INVENTION

This invention relates generally to ultrasound systems and, more particularly, to a motor driver for controlling ultrasound probes for ultrasound imaging systems, especially portable ultrasound medical imaging systems.

Ultrasound systems typically include ultrasound scanning devices, such as ultrasound probes having transducers that allow for performing various ultrasound scans (e.g., imaging a volume or body). The ultrasound probes are typically connected to an ultrasound system for controlling the operation of the probes. The probes include a scan head having a plurality of transducer elements (e.g., piezoelectric crystals), which may be arranged in an array. The ultrasound system drives the transducer elements within the array during operation, such as during a scan of a volume or body, which may be controlled based upon the type of scan to be performed. In addition to electrically driving the transducer elements, the ultrasound system also may control mechanical movement of the transducer elements within the probe. The ultrasound system may include a plurality of channels for communicating with the probe. For example, the channels may transmit pulses for driving the transducer elements and for receiving signals therefrom. Additionally, control signals may be used to control the mechanical movement of the transducer array within the probe.

In volume probes, for example three-dimensional (3D) or four-dimensional (4D) probes, wherein the scan head moves during scan operation, and more particularly, wherein the transducer elements move, a motor controller is used to control the movement of the transducer elements within the scan head. For example, the motor controller may control the swinging or rotating of the transducer elements about an axle within the scan head based on signals received from the ultrasound system. The motor controller controls the translation of power from a motor to the scan head to control movement of the transducer elements.

Portable ultrasound systems, which have increasingly smaller footprints, often include an entire ultrasound system (e.g., processing components, etc.) embodied within a housing having the dimensions of a typical laptop computer or smaller. An ultrasound probe is connected to the portable ultrasound system, which then controls the probe to perform an ultrasound scan. Because of the smaller size of a portable ultrasound system, space for the various components can be more limited. Accordingly, system components may have to be implemented in smaller areas, which can result, for example, in having less processing or storage capabilities, thereby possibly reducing the performance of the overall system. Moreover, portable systems may also have other limitations, such as power and heat constraints. For example, because a portable system may run for extended periods of time on battery power, more efficient or decreased power consumption is often desirable in order to increase the time of use between battery charges. Additionally, the heat generated within smaller portable systems by the various components can also decrease the performance of the overall system. Thus, heat dissipation, or reduction of heat generation by the various components, is important.

Additionally, in volume probes having moving transducer arrays, a significant amount of power is needed and consumed by the motor and motor controller in order to move the transducer array within the scan head. Thus, as the amount of available power decreases, for example, in portable systems using battery power instead of 120 volt power wall supplies, large consumers of power, such as the motor controller, can decrease the useful operation of the system between charges. In addition, the power provided by a battery may also be insufficient to operate the motor. Moreover, known linear motor controllers or drivers are large, such that the reduced footprint of portable ultrasound systems cannot accommodate these linear motors controllers or drivers because of the space required for other components (e.g., processors, beamformers, power supplies, user interfaces, etc.). Additional space can also be needed for cooling components, e.g., to cool the motor controller or driver.

BRIEF DESCRIPTION OF INVENTION

In accordance with one embodiment, an ultrasound system is provided that includes a transmitter and receiver both communicatively coupled to a transducer array of an ultrasound probe. The ultrasound system further includes a digital motor driver for controlling movement of the transducer array.

In accordance with another embodiment, a portable ultrasound system is provided that includes a volume probe having a motor to move a scan head including a transducer array. The portable ultrasound system further includes a motor controller and a digital motor driver connected to the motor controller and configured to receive control signals from the motor controller to drive the motor of the volume probe to move the scan head.

In accordance with yet another embodiment, a method of controlling an ultrasound probe is provided. The method includes powering a digital motor driver to drive a motor of the probe. The method further includes controlling movement of a scan head within the probe using the digital motor driver.

DETAILED DESCRIPTION OF VARIOUS PREFERED EMBODIMENTS

The foregoing summary, as well as the following detailed description of certain embodiments of the inventive arrangements, will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or random access memory, hard disk, or the like). Similarly, the programs may be stand alone programs, may be incorporated as subroutines in an operating system, may be functions in an installed software package, and the like. It should be understood that the various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" of the inventive arrangements are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

It should be noted that although the various embodiments may be described in connection with an ultrasound system, the methods and systems described herein are not limited to ultrasound imaging. In particular, the various embodiments may be implemented in connection with different types of medical imaging, including, for example, magnetic resonance imaging (MRI) and computed-tomography (CT) imaging. Further, the various embodiments may be implemented in other non-medical imaging systems, for example, non-destructive testing systems.

Exemplary embodiments of ultrasound systems including a motor controller and motor driver are described in detail below. The motor controller and motor driver are configured to control the operation of a motor that causes a transducer array in an ultrasound probe of the ultrasound system to move. The motor driver in the various embodiments is a digital motor driver having a switch amplifier (also known as a digital amplifier) for use in controlling the movement of the transducer array.

Figure 1:
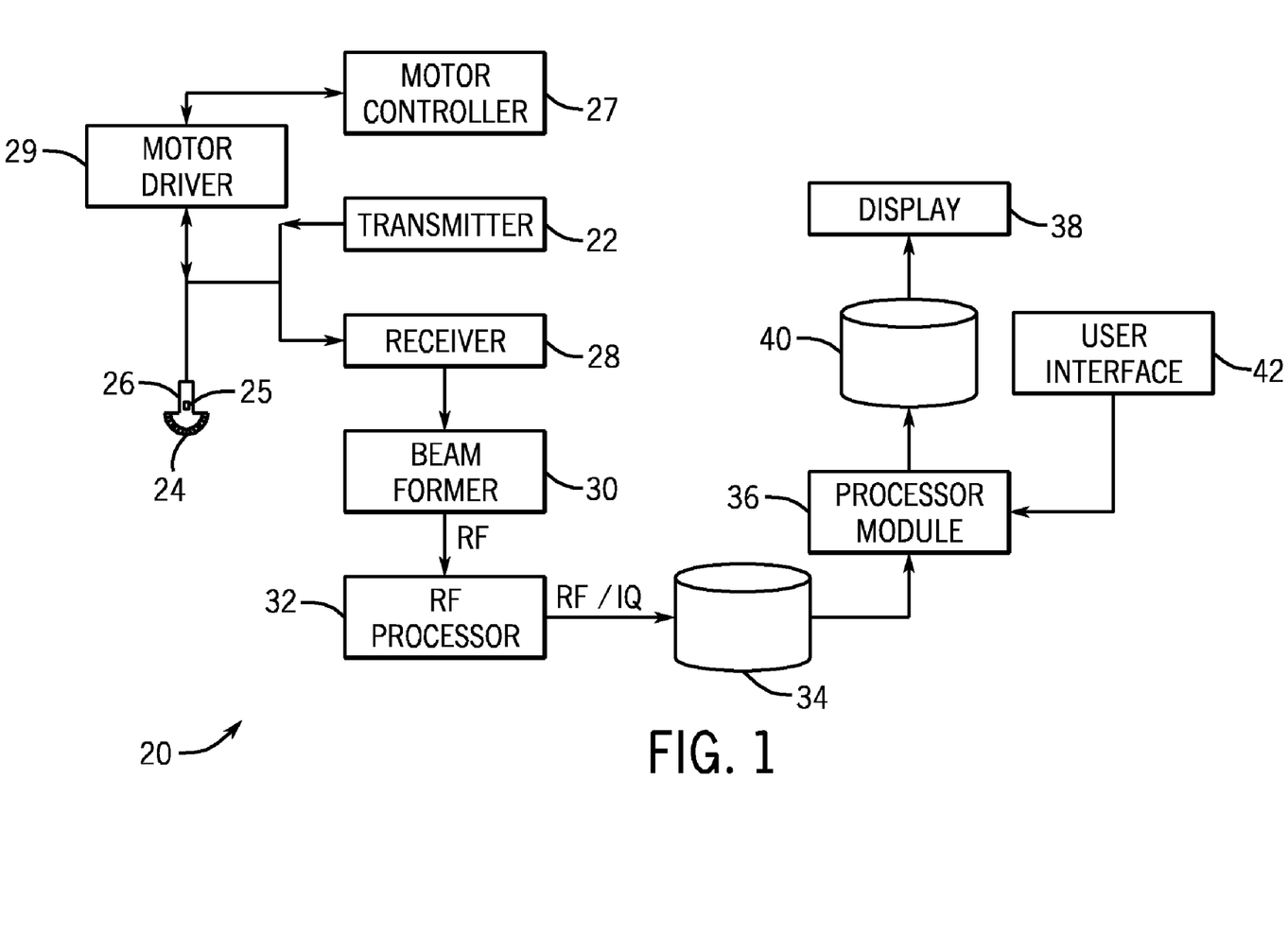
FIG. 1 is a block diagram of an ultrasound system formed in accordance with an exemplary embodiment of the inventive arrangements.

FIG. 1 illustrates a block diagram of an ultrasound system 20 formed in accordance with various embodiments of the inventive arrangements. The ultrasound system 20 includes a transmitter 22 that drives an array of elements 24 (e.g., piezoelectric crystals) within a transducer 26 to emit pulsed ultrasonic signals into a body or volume. A variety of geometries may be used, and the transducer 26 may be provided as part of, for example, different types of ultrasound probes. For example, the ultrasound probe may be a volume probe, such as a three-dimensional (3D) probe or a four-dimensional (4D) probe wherein the array of elements 24 can be mechanically moved. The array of elements 24 may be swept or swung about an axis powered by a motor 25. In these embodiments, movement of the array of elements 24 is controlled by a motor controller 27 and motor driver 29. The motor controller 27 and motor driver 29 are described in more detail below.

The emitted pulsed ultrasonic signals are back-scattered from structures in a body, for example, blood cells or muscular tissue, to produce echoes that return to the array of elements 24. The echoes are received by a receiver 28. The received echoes are provided to a beamformer 30 that performs beamforming and outputs an RF signal. The RF signal is then provided to an RF processor 32 that processes the RF signal. Alternatively, the RF processor 32 may include a complex demodulator (not shown) that demodulates the RF signal to form IQ data pairs representative of the echo signals. The RF or IQ signal data may then be provided directly to a memory 34 for storage (e.g., temporary storage).

The ultrasound system 20 also includes a processor module 36 to process the acquired ultrasound information (e.g., RF signal data or IQ data pairs) and prepare frames of ultrasound information for display on a display 38. The processor module 36 is adapted to perform one or more processing operations according to a plurality of selectable ultrasound modalities on the acquired ultrasound information. Acquired ultrasound information may be processed in real-time during a scanning session as the echo signals are received. Additionally or alternatively, the ultrasound information may be stored temporarily in the memory 34 during a scanning session and processed in less than real-time in a live or off-line operation. An image memory 40 is included for storing processed frames of acquired ultrasound information that are not scheduled to be displayed immediately. The image memory 40 may comprise any known data storage medium, for example, a permanent storage medium, removable storage medium, etc.

The processor module 36 is connected to a user interface 42 that controls operation of the processor module 36 as explained below in more detail and is configured to receive inputs from an operator. The display 38 includes one or more monitors that present patient information, including diagnostic ultrasound images to the user for review, diagnosis, and/or analysis. The display 38 may automatically display, for example, one or more planes from a 3D ultrasound data set stored in the memory 34 or 40. One or both of the memories 34, 40 may store 3D data sets of the ultrasound data, where such 3D data sets are accessed to present 2D and 3D images. For example, a 3D ultrasound data set may be mapped into the corresponding memory 34 or 40, as well as one or more reference planes. The processing of the data, including the data sets, is based, at least in part, on user inputs, for example, user selections received at the user interface 42.

In operation, the ultrasound system 20 acquires data, for example, volumetric data sets by various techniques (e.g., 3D scanning, real-time 3D imaging, volume scanning, 2D scanning with transducers having positioning sensors, freehand scanning using a voxel correlation technique, scanning using 2D or matrix array transducers, etc.). The data may be acquired by mechanically moving the array of elements 24 of the transducer 26, for example, by performing a sweeping type of scan. The transducer 26 also may be moved manually, such as along a linear or arcuate path, while scanning a region of interest (ROI). At each linear or arcuate position, the transducer 26 obtains scan planes that are stored in the memory 34.

Figure 2:
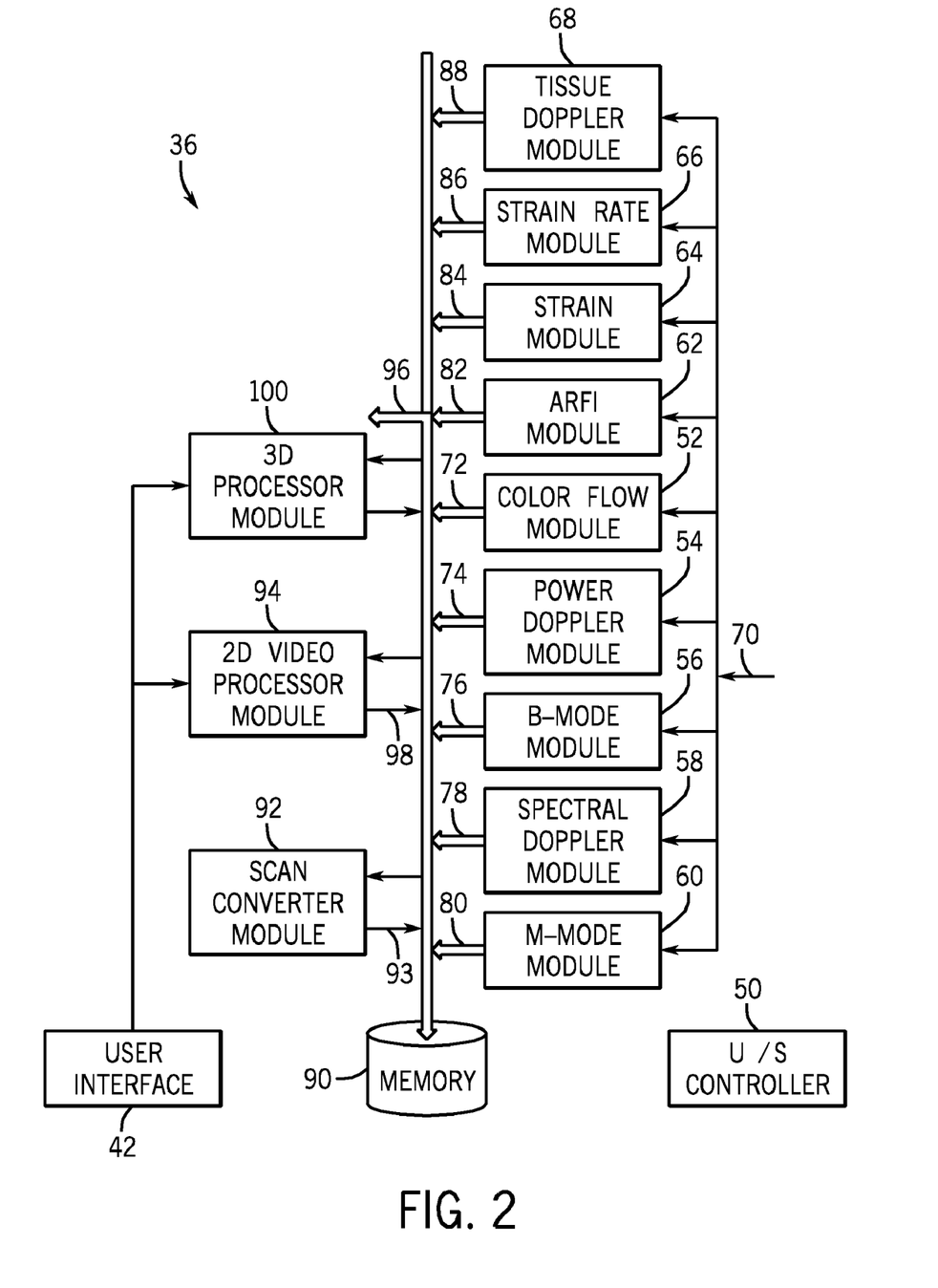
FIG. 2 is a block diagram of the ultrasound processor module of FIG. 1 formed in accordance with an exemplary embodiment of the inventive arrangements.

FIG. 2 illustrates an exemplary block diagram of the processor module 36 of FIG. 1. The processor module 36 is illustrated conceptually as a collection of sub-modules, but it may also be implemented utilizing any combination of dedicated hardware boards, digital signal processors (DSPs), processors, etc. Alternatively, the sub-modules of FIG. 2 may be implemented utilizing an off-the-shelf PC with a single processor or multiple processors, with functional operations distributed between processors. As a further option, the sub-modules of FIG. 2 may also be implemented utilizing a hybrid configuration, in which certain modular functions are performed utilizing dedicated hardware, while the remaining modular functions are performed utilizing an off-the-shelf PC and/or the like. The sub-modules also may be implemented as software modules within a processing unit.

The operations of the sub-modules illustrated in FIG. 2 may be controlled by a local ultrasound controller 50 or by the processor module 36. The sub-modules 52-68 perform mid-processor operations. The ultrasound processor module 36 may receive ultrasound data 70 in one of several forms. In the embodiment of FIG. 2, for example, the received ultrasound data 70 constitutes IQ data pairs representing the real and imaginary components associated with each data sample. The IQ data pairs are provided, for example, to one or more of a color-flow sub-module 52, a power Doppler sub-module 54, a B-mode sub-module 56, a spectral Doppler sub-module 58, and an M-mode sub-module 60. Other sub-modules may also be included, such as an Acoustic Radiation Force Impulse (ARFI) sub-module 62, a strain sub-module 64, a strain rate sub-module 66, a Tissue Doppler (TDE) sub-module 68, among others.

Each of sub-modules 52-68 are configured to process the IQ data pairs in a corresponding manner to generate color-flow data 72, power Doppler data 74, B-mode data 76, spectral Doppler data 78, M-mode data 80, ARFI data 82, echocardiographic strain data 84, echocardiographic strain rate data 86, and tissue Doppler data 88, all of which may be stored in a memory 90 (or memory 34 or image memory 40 shown in FIG. 1) temporarily before subsequent processing. The data 72-88 may be stored, for example, as sets of vector data values, where each set defines an individual ultrasound image frame. The vector data values are generally organized based on the polar coordinate system.

A scan converter sub-module 92 accesses and obtains from the memory 90 the vector data values associated with an image frame and converts the set of vector data values to Cartesian coordinates to generate an ultrasound image frame 93 formatted for display. The ultrasound image frames 93 generated by the scan converter sub-module 92 may be provided back to the memory 90 for subsequent processing or may be provided to the memory 34 or image memory 40.

Once the scan converter sub-module 92 generates the ultrasound image frames 93 associated with the data, the image frames may be restored in the memory 90 or communicated over a bus 96 to a database (not shown), the memory 34, the image memory 40, and/or to other processors (not shown).

A 2D video processor sub-module 94 may be used to combine one or more of the frames generated from the different types of ultrasound information. For example, the 2D video processor sub-module 94 may combine different image frames by mapping one type of data to a gray map and mapping the other type of data to a color map for video display. In the final displayed image, the color pixel data is superimposed on the gray scale pixel data to form a single multi-mode image frame 98 that is again re-stored in the memory 90 or communicated over the bus 96. Successive frames of images may be stored as a cine loop in the memory 90 or memory 40 (shown in FIG. 1). The cine loop represents a first in, first out circular image buffer to capture image data that is displayed in real-time to the user, such as one or more heart cycles. The user may freeze the cine loop by entering a freeze command at the user interface 42. The user interface 42 may include, for example, a keyboard, mouse, trackball, and/or any or all other input controls associated with inputting information into the ultrasound system 20 (shown in FIG. 1).

A 3D processor sub-module 100 is also controlled by the user interface 42 and accesses the memory 90 to obtain spatially consecutive groups of ultrasound image frames (that may be acquired, for example, by a sweeping ultrasound scan) and to generate three dimensional image representations thereof, such as through volume rendering or surface rendering algorithms, as are known. The three-dimensional images may be generated utilizing various imaging techniques, such as ray-casting, maximum intensity pixel projection, and/or the like. Additionally, the three-dimensional images may be displayed over time, thereby providing four-dimensional operation, as is known.

Figure 3:
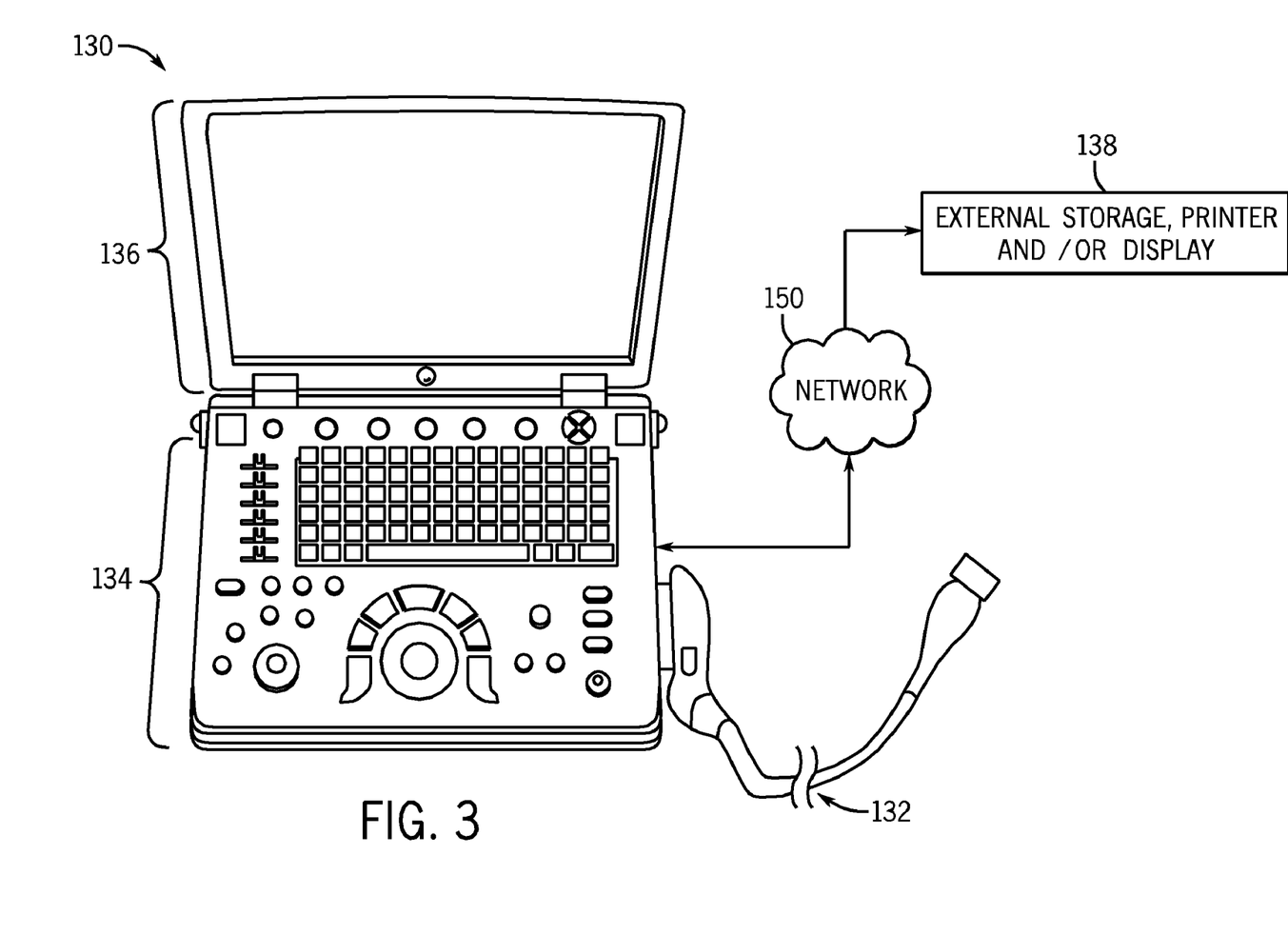
FIG. 3 is a top perspective view of a miniaturized ultrasound imaging system formed in accordance with an exemplary embodiment of the inventive arrangements that may be used to control a volume probe.

Various embodiments of the inventive arrangements can also be implemented in a 3D or 4D-capable miniaturized ultrasound imaging system 130, as shown in FIG. 3, that controls a connected volume probe 132 (having moving transducer elements). For example, the volume probe 132 may have a 2D array of elements 24 as discussed previously with respect to the transducer 26 of FIG. 1. A user interface 134 (that may also include an integrated display 136) is provided to receive commands from an operator. As used herein, "miniaturized" generally means that the ultrasound system 130 is a handheld or hand-carried device and/or is configured to be carried in a person's hand, pocket, briefcase-sized case, backpack, and/or the like. For example, the miniaturized ultrasound imaging system 130 may be a hand-carried device having a size of a typical laptop computer, for instance, having dimensions of approximately 2.5 inches in depth, approximately 14 inches in width, and approximately 12 inches in height. The miniaturized ultrasound imaging system 130 may be, for example, a Voluson i compact 4D ultrasound system available from G.E. Healthcare in Waukesha, Wis., and having an available space for components of 300 millimeters (mm)×270 mm×35 mm. Thus, the miniaturized ultrasound imaging system 130 may include a housing with available space of 2,835,000 mm$^3$ in which space the various components can be provided.

The miniaturized ultrasound imaging system 130 may weigh about ten pounds or less and be easily portable by the operator. The integrated display 136 (e.g., an internal display) is also provided and configured to display a medical image.

Ultrasonic data from the miniaturized ultrasound imaging system 130 may be sent to an external device 138 via a wired or wireless network 150 (or direct connection, for example, via a serial or parallel cable or USB port). In some embodiments, the external device 138 may be a computer or a workstation having a display. Alternatively, the external device 138 may be a separate external display or a printer capable of receiving image data from the miniaturized ultrasound imaging system 130 and of displaying or printing images that may have greater resolution than the integrated display 136.

Figure 4:
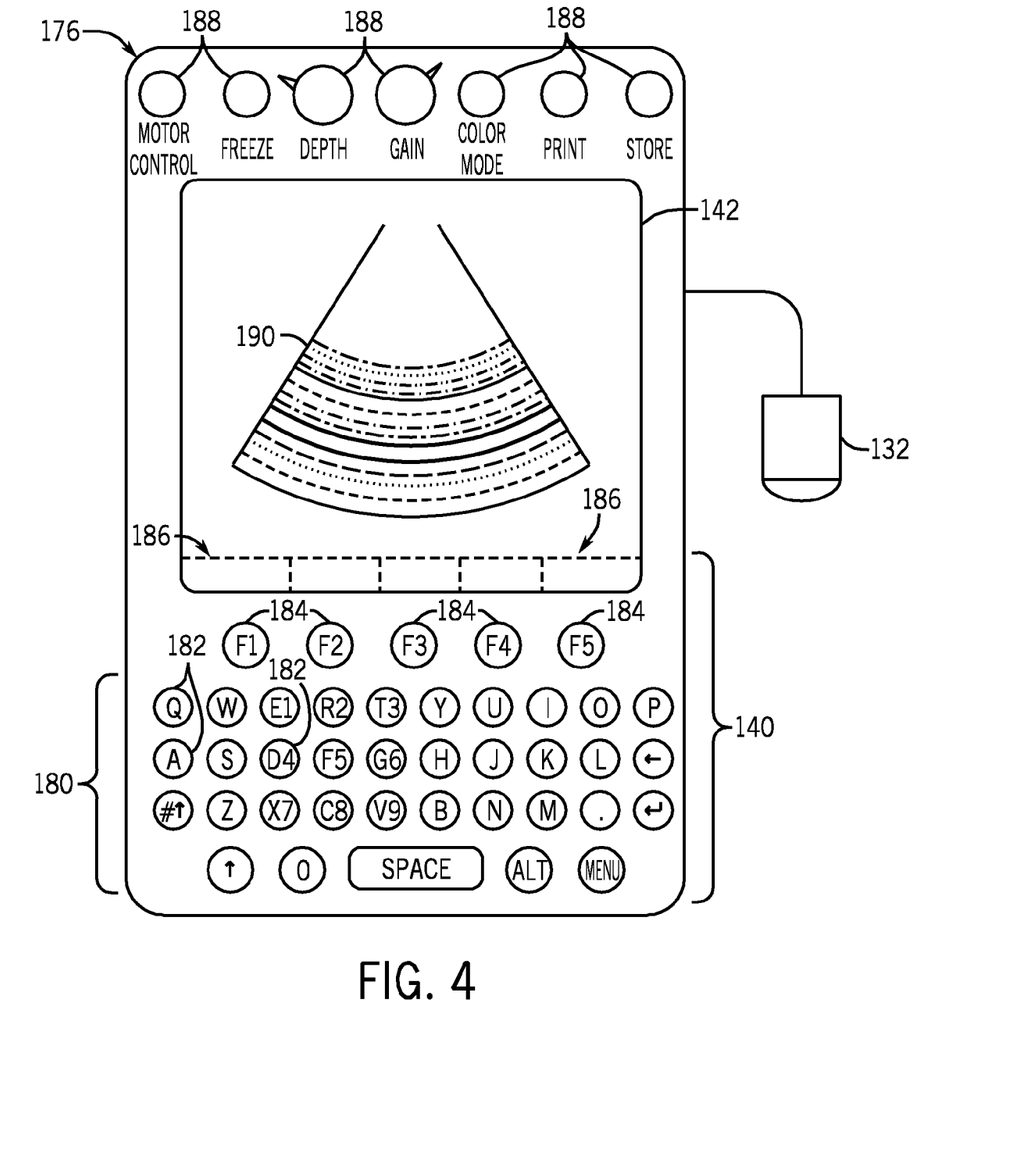
FIG. 4 is a top view of a hand carried or pocket-sized ultrasound imaging system formed in accordance with an exemplary embodiment of the inventive arrangements that may be used to control a volume probe.

However, it should be noted that the various embodiments may be implemented in connection with ultrasound systems having different sizes and shapes. For example, a hand carried or pocket-sized ultrasound imaging system 176 may also be provided, as shown in FIG. 4. In that system 176, a display 142 and user interface 140 may form a single unit. By way of example, such a system 176 may be a pocket-sized or hand-sized ultrasound system that can be approximately 2 inches wide, approximately 4 inches in length, and approximately ½ inches in depth, and/or weigh less than 3 ounces. The display 142 may be, for example, a 320×320 pixel color LCD display (on which a medical image 190 can be displayed). A typewriter-like keyboard 180 of buttons 182 may optionally be included as part of the user interface 140. It should be noted that the various embodiments may be implemented in connection with a pocket-sized ultrasound system 176 having different dimensions, weights, and/or power consumptions.

Multi-function controls 184 may also be assigned functions in accordance with a mode of system operation. As a result, for example, each of the multi-function controls 184 may be configured to provide a plurality of different actions. Label display areas 186 can be associated with the multi-function controls 184 and included as necessary and/or desired on the display 142. The system 176 may also have additional keys and/or controls 188 for special purpose functions, which may include, for example, but are not limited to "motor control," "freeze," "depth control," "gain control," "color-mode," "print," and "store," etc.

Figure 5:
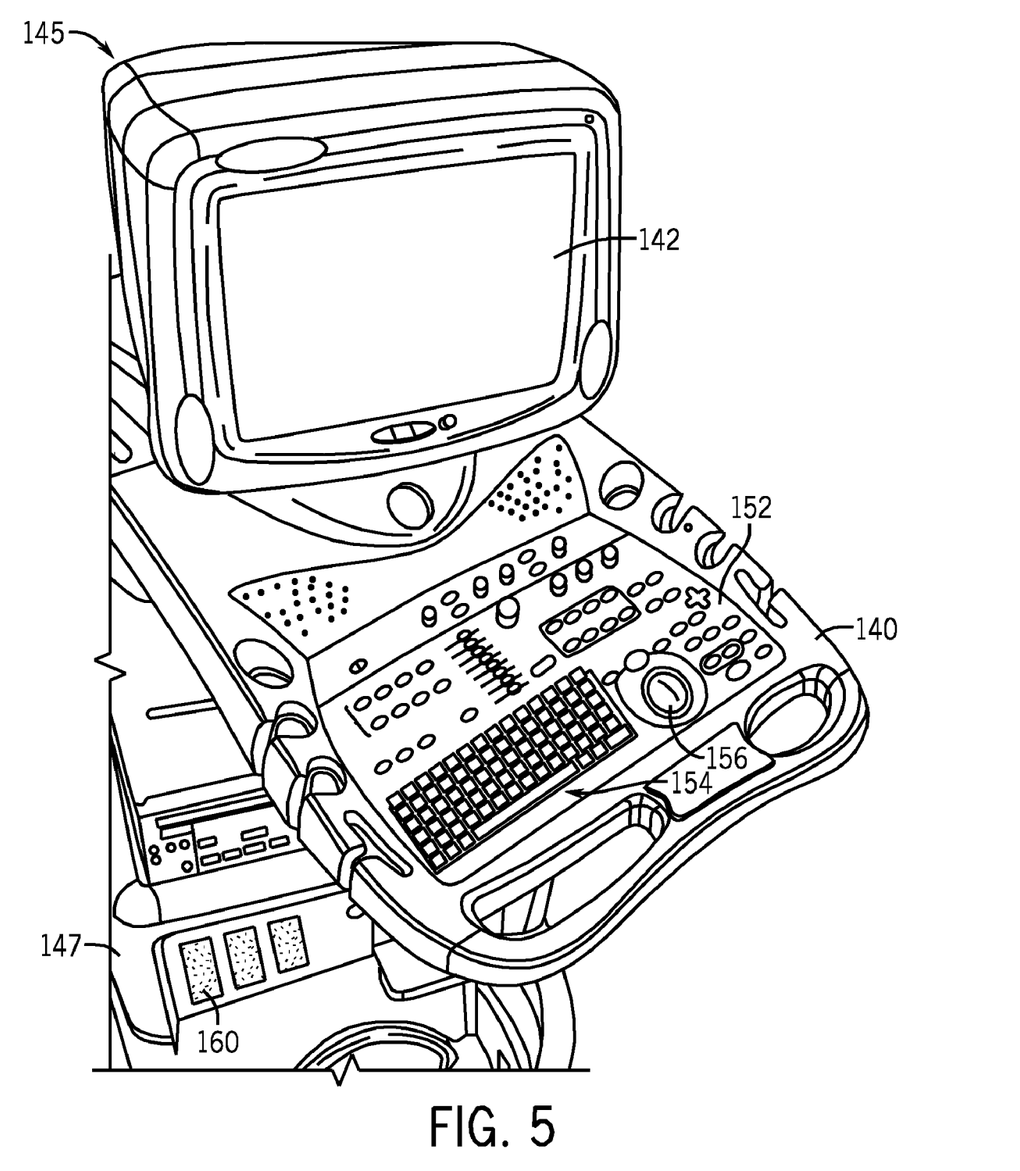
FIG. 5 is a side perspective view of a console-based ultrasound imaging system formed in accordance with an exemplary embodiment of the inventive arrangements that may be used to control a volume probe.

The various embodiments are not limited to miniaturized or portable imaging systems 176, but they may also be implemented in larger systems, for example, in a console-based ultrasound imaging system 145 shown in FIG. 5 and provided on a movable base 147. Such a system 145 may be referred to as a cart-based system. In any event, a display 142 and user interface 140 can again be provided, and it should be understood that the display 142 may be separate and/or separable from the user interface 140. The user interface 140 may also optionally be a touchscreen, allowing the operator to select options by touching displayed graphics, icons, and the like.

The user interface 140 may also include control buttons 152 that may be used to control the system 145 as desired and/or needed, and/or as typically provided. The user interface 140 may provide multiple interface options that the user may physically manipulate to interact with ultrasound data and other data that may be displayed, as well as to input information and to set and change scanning parameters, such as the sweeping operation of transducer arrays. The interface options may be used for specific inputs, programmable inputs, contextual inputs, and the like. For example, a keyboard 154 and track ball 156 may be provided. The system 145 may also have at least one probe port 160 for accepting probes.

Figure 6:
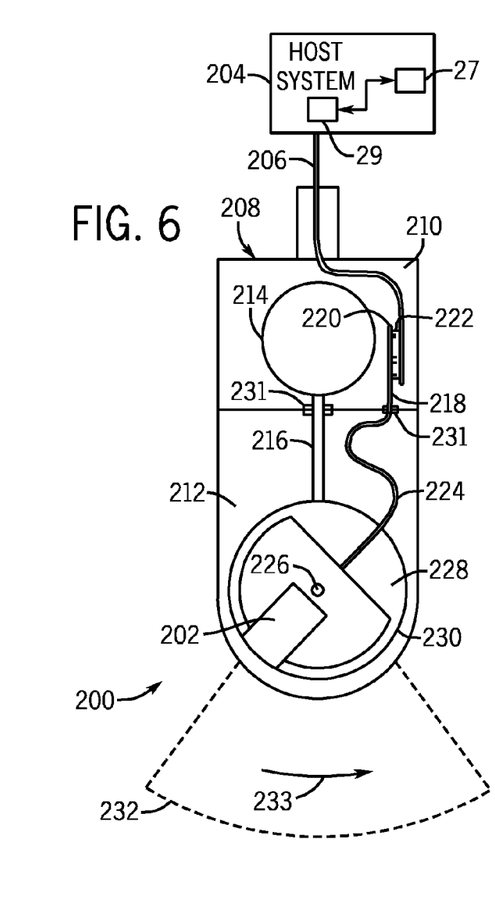
FIGS. 6-8 are cross-sectional elevation views of a volume probe in accordance with an exemplary embodiment of the inventive arrangements showing a moving scan head that may be controlled by the ultrasound systems shown in FIGS. 1-5.
Figure 7:
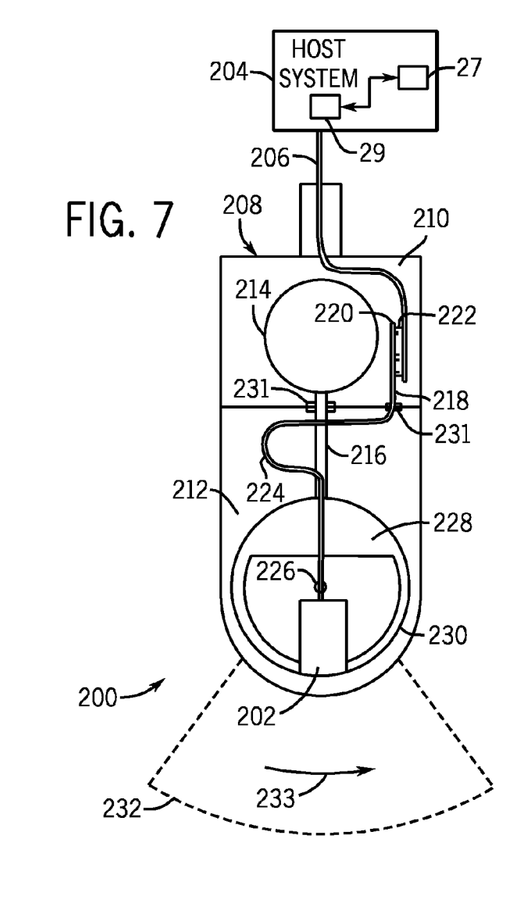
Figure 8:
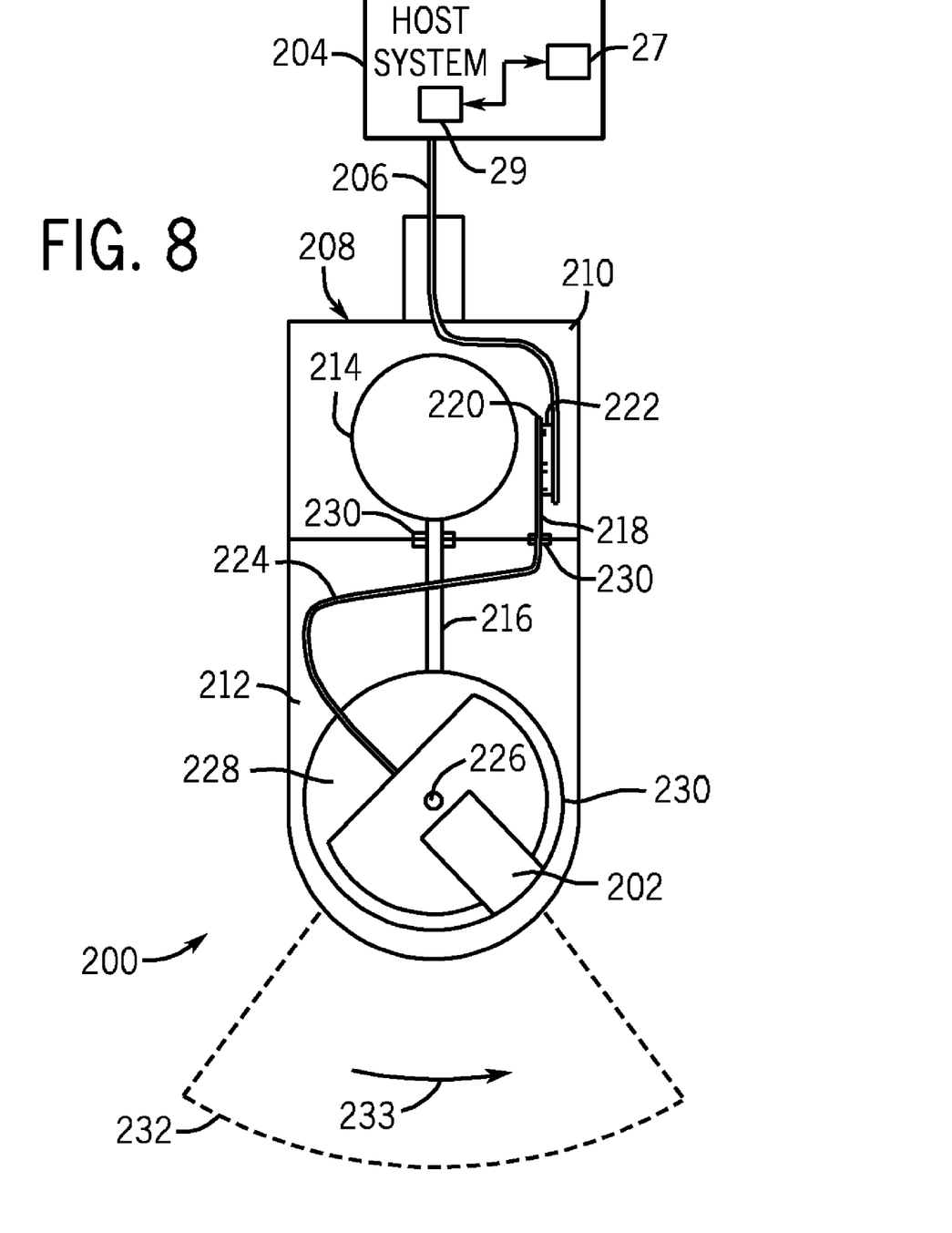

Now then, FIGS. 6-8 illustrate an exemplary volume imaging ultrasound probe 200 having a transducer array 202, which may be, for example, the array of elements 24 shown in FIG. 1. The volume imaging ultrasound probe 200 is in communication with a host system 204 (e.g., an ultrasound scanner or ultrasound laptop) via a system cable 206. The host system 204 may include some or all of the components of the ultrasound system 20 shown in FIG. 1, including the motor controller 27 and motor driver 29 that control the mechanical movement of the transducer array 202. The probe 200 also preferably includes a housing 208 having a first chamber 210 (e.g., a dry chamber) and a second chamber 212 (e.g., a wet chamber). The first chamber 210 and second chamber 212 may be formed as a single unit (e.g., unitary construction) or as separate units connected together. In an exemplary embodiment, the first chamber 210 is a dry or air chamber having contained therein drive means for mechanically controlling the transducer array 202 and communication means for electrically controlling the transducer array 202.

The drive means generally includes a motor 214 (e.g., stepper motor) and a gear arrangement 216, such as a single axle or a two-stage gear arrangement having a belt drive and a rope drive. The communication means generally includes one or more communication lines, for example, configured as one or more flexible printed circuit boards 218 that connect at one end to the system cable 206, for example, via rigid printed circuit boards 220 connected to connection members 222, and at the other end to the coaxial cables 224. The communication means thereby provides communication between the transducer array 202 and host system 204.

It should be noted that although the drive means and communication means are described herein having specific component parts, the drive means and communication means are not so limited. For example, the drive means may have a different gear arrangement and the communication means may have different connection members or transmission lines.

In this exemplary embodiment, the second chamber 212 is a wet chamber (e.g., chamber having acoustic liquid therein) having contained therein transducer driving means for moving (e.g., rotating or swinging) the transducer array 202 and transducer control means for selectively driving elements of the transducer array 202 (e.g., the piezoelectric ceramics). The transducer driving means generally includes a drive shaft 226 in connection with a scan head housing 228, supported, for example, on brackets (not shown), that operates to move the transducer array 202 as part of a scan head 230 when driven by the drive means. A support member (not shown) also may be provided for supporting the scan head housing 228 and a biasing spring (not shown) may be provided, for example, to ensure proper tension on the drive means and transducer drive means. It should be noted that an acoustic membrane (not shown) may be provided surrounding the scan head housing 228 and formed as part of the housing 208. The transducer control means generally includes the coaxial cables 224 (e.g., three layers of sixty-four coaxial cables) and/or flexible printed circuit board 218, and optionally multiplexing circuits (not shown) connected to the transducer array 202. The communication means are connected to the transducer driving means using any suitable connector, such as a complimentary pin connector arrangement.

It should be noted that although the transducer driving means and transducer control means are described herein having specific component parts, the transducer driving means and the transducer control means are not so limited. For example, the transducer driving means may have a different shaft arrangement and the transducer control means may have different control circuits or transmission lines. It also should be noted that additional or different component parts may be provided in connection with the volume imaging ultrasound probe 200 as needed or desired, and/or based upon the particular type and application of probe 200. For example, a lens covering the transducer array 202 may be provided based upon the type of volume imaging ultrasound probe 200.

It should be noted that one or more seals members 231 may be provided between the first chamber 210 and second chamber 212 to provide a liquid tight sealing arrangement between the first chamber 210 and second chamber 212. Different configurations of sealing arrangements are contemplated. For example, one or more slots or openings (not shown) may be provided as part of a bracket member (not shown) with a sealing element 231 (e.g., rubber gasket and aluminum plate) ensuring proper sealing between the first chamber 210 and second chamber 212.

In operation, and as described in more detail below, the motor controller 27 and motor driver 29 control the mechanical movement of the scan head 230, which is powered by the motor 214. Control signals may be conveyed, for example, using the system cable 206 to control the operation of the motor 214. The scan head 230 is accordingly operated in a swinging or rotating manner, as indicated by arrows 233 shown in FIGS. 6-8 (with the scan head 230 in different positions) to provide, for example, a sweeping scan 232. It should be noted that the transducer array 202 may be configured for operation in different modes, such as, for example, a 1D, 1.25D, 1.5D, 1.75D, 2D, 3D, and/or 4D modes of operation.

Figure 9:
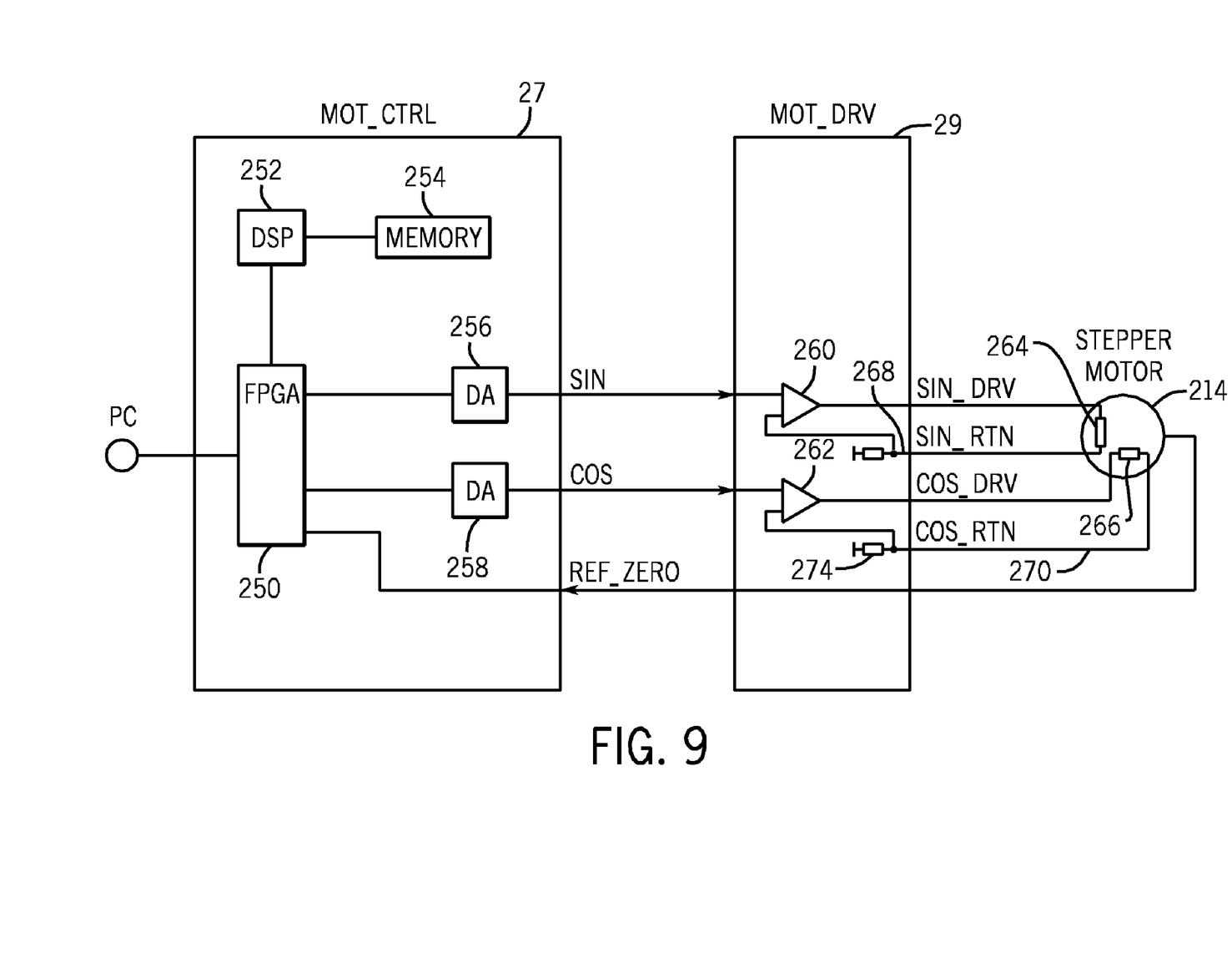
FIG. 9 is a simplified block diagram of a motor controller and a motor driver formed in accordance with an exemplary embodiment of the inventive arrangements.

Various embodiments of the inventive arrangements provide the motor controller 27 for controlling a motor driver 29, as shown in FIG. 9. The motor driver 29 in the various embodiments is preferably a digital motor driver that uses less space within the ultrasound system housing and provides control signals to the motor 214, which controls the movement of the scan head 230. It should be noted that although the motor controller 27 and motor driver 29 are shown as different components, the motor controller 27 and motor driver 29 may also be provided as a single unit.

FIG. 9 is a simplified block diagram of the motor controller 27 and motor driver 29. Preferably, the motor controller 27 includes a programmable logic component, for example, a field-programmable gate array (FPGA) 250 connected to a processor, for example, a processor with the ultrasound system 20 (shown in FIG. 1) or a processor within a miniaturized portable system. Preferably, the FPGA 250 is connected to a digital signal processor 252 that is connected to a memory 254. The FPGA 250 is also connected to a first digital to analog converter 256 and a second digital to analog converter 258. The first and second digital to analog converters 256, 258 output separate control signals, for example, sine and cosine wave control signals, respectively, to the motor driver 29, as described in more detail below. For example, a sine wave and a ninety degree shifted cosine wave may be generated.

The motor driver 29 includes a first differential amplifier 260 and a second differential amplifier 262 for receiving, for example, the sine and cosine wave control signals, respectively, from the first and second digital to analog converters 256, 258 of the motor controller 27. The first and second differential amplifiers 260, 262 operate as error amplifiers with one input of the differential inputs receiving the respective control signal from the motor controller 27 (e.g., the sine and cosine wave control signals) and the other input of the differential inputs receiving a feedback signal from a first coil 264 and a second coil 266, respectively, of the motor 214. Feedback paths 268, 270 include feedback resistors 272, 274, respectively, connected to ground. The feedback paths 268, 270 and feedback resistors 272, 274 allow measurement of current through the first and second coils 264, 266 of the motor 214.

Accordingly, the motor driver 29 operates as a switch amplifier (or digital or power amplifier), wherein the current through the motor 214 is sensed and compared with an incoming voltage, for example, as defined by the sine and cosine wave control signals. Thus, incoming voltage control signals and feedback signals are compared to measure an error, which is then used to control the voltage applied to the first and second coils 264, 266 of the motor 214, and thereby control mechanical movement of the scan head 230 (shown in FIGS. 6-8) that is moved by the motor 214. As described in more detail below, the speed of movement is defined by the frequency of the control signals (e.g., the sine and cosine wave control signals) and the direction of movement defined by the phase difference between the control signals.

Figure 10:
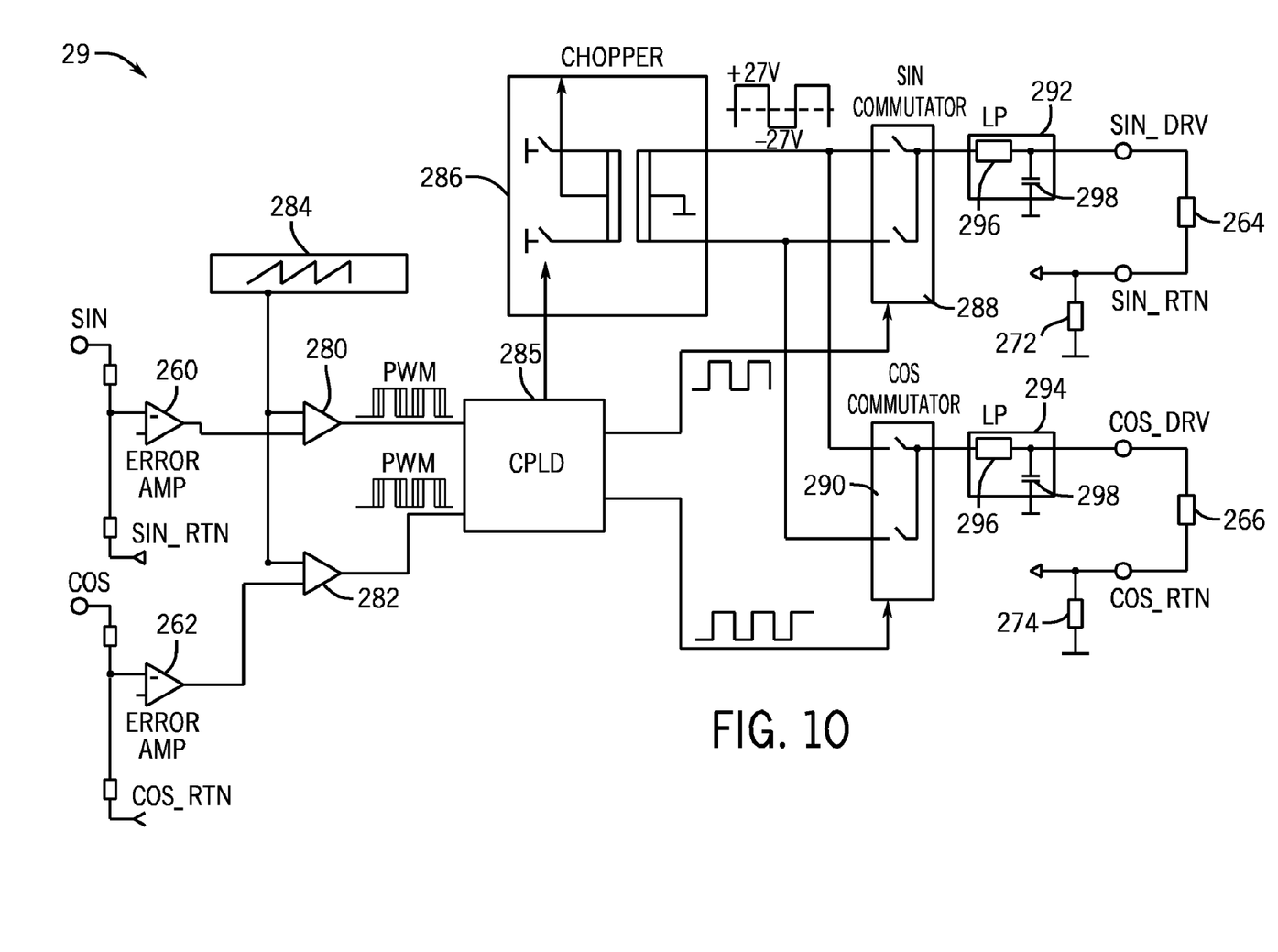
FIG. 10 is a detailed block diagram of a motor driver formed in accordance with an exemplary embodiment of the inventive arrangements.

Referring now to FIG. 10, a more detailed diagram of one embodiment of the motor driver 29 is shown. In particular, each of the outputs of the first and second differential amplifiers 260, 262 are connected to one input of a first comparator 280 and a second comparator 282, respectively. The other input of the first and second comparators 280, 282 are connected to a pulse generator 284 that generates, for example, a saw-wave signal. The first and second comparators 280, 282 compare the respective inputs and each generates a pulse width modulated output. The first and second comparators 280, 282 compare the voltages at the inputs and switch the output signal based on which of the inputs is larger.

Each of the outputs of the first and second comparators 280, 282 are connected to a complex programmable logic device (CPLD) 285. The CPLD 285 is connected to a chopper circuit, and more particularly, a chopper amplifier 286. The chopper amplifier 286 is a switching device that, in this embodiment, operates as a DC amplifier. In particular, from an input DC voltage from the CPLD 285, the chopper amplifier 286 generates an amplified rectangular output signal. The output of the chopper amplifier 286 is connected to and drives both a first commutator 288 and a second commutator 290. For example, from an input DC voltage of about 11 volts to 12 volts (or any typical voltage from a rechargeable battery), the chopper amplifier 286 generates an amplified fifty percent duty cycle rectangular wave, for example, a plus or minus twenty-seven volt rectangular wave signal.

In this embodiment, the first commutator 288 is a sine commutator and the second commutator 290 is a cosine commutator. Each of the first and second commutators 288, 290 receive a control signal (e.g., rectangular pulse signal) from the CPLD 285 based on, for example, the sine and cosine control signals, respectively. The output of each of the first and second commutators 288, 290 is connected to a first low pass filter 292 and a second low pass filter 294, respectively. The first and second low pass filters 292, 294 each include an inductor 296 and a capacitor 298. The outputs of the first and second low pass filters 292, 294 are connected to the first and second coils 264, 266 of the motor 214 (shown in FIG. 9), respectively. It should be noted that the first and second commutators 288, 290 invert the polarity of the input signal that each of the first and second commutators 288, 290 receive. It also should be noted that the phase of the signals from the first and second commutators 288, 290 to the first and second low pass filters 292, 294 controls the output voltage of the first and second low pass filters 292, 294.

Figure 11:
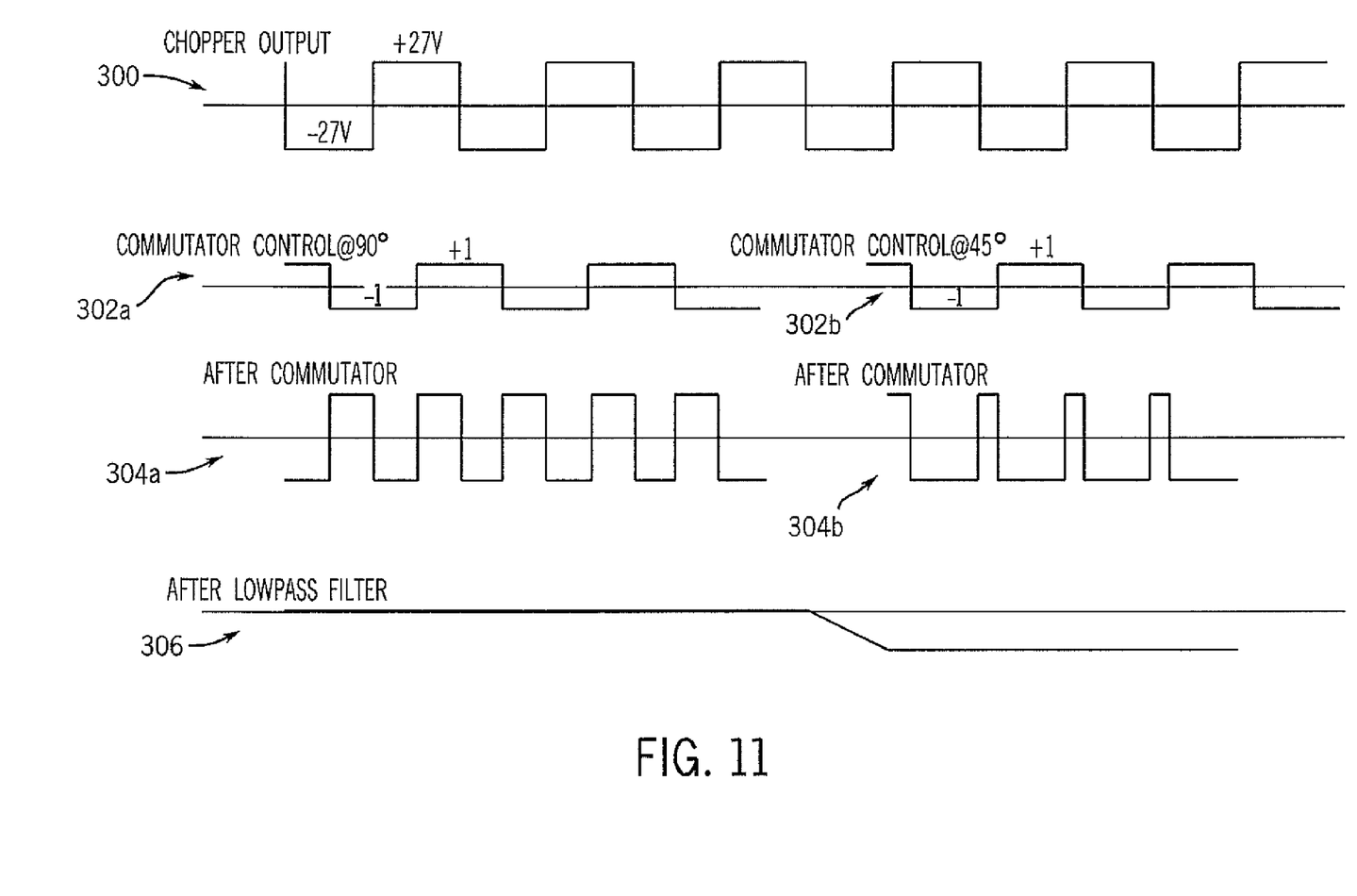
FIG. 11 is a signal traces diagram of exemplary signals used in the motor controller and motor driver of FIGS. 9-10 that may be used to control a volume probe.

Control signals from the motor controller 27 are used by the motor driver 29 to generate voltages to drive the operation of the motor 214, and in particular, the speed of movement of the motor 214 and the direction of movement of the motor 214, for example, in which direction and how fast the scan head 230 (shown in FIGS. 6-8) swings. Exemplary signals at various points within the motor driver 29 are illustrated in FIG. 11. For example, a chopper output signal 300 represents the output signal from the chopper amplifier 286, which, in one embodiment, is a plus or minus twenty-seven volt rectangular wave signal. Commutator control signals 302a, 302b represent signals generated by the CPLD 285 and provided to each of the first and second commutators 288, 290. One commutator control signal 302a is shifted ninety degrees with respect to the chopper output signal 300 and the other commutator control signal 302b is shifted forty-five degrees with respect to the chopper output signal 300. Corresponding commutator output signals 304a, 304b from the first and second commutators 288, 290 are also generated, as shown. The commutator output signals 304a, 304b are essentially the chopper output signal 300 multiplied by the commutator control signals 302a, 302b (e.g., the multiplication of two rectangular waveforms) and is provided to the low pass filters 292, 294. As can be seen in this example, one commutator output signal 304a has a fifty percent duty cycle with twice the frequency of one of the commutator control signals 302a, and the other commutator output signal 304b has a seventy-five percent low and twenty-five percent high duty cycle. The commutator output signals 304a, 304b result in a voltage output 306 from the first and second low pass filters 292, 294 and that drives the first and second coils 264, 266 of the motor 214. One of the commutator output signals 304a drives the output to a zero voltage and the other 304b drives the output to a negative voltage. Thus, a zero percent duty cycle can be generated by control signals from the CPLD 285 that are not shifted and a one-hundred percent duty cycle can be generated by control signals that are shifted by 180 degrees.

Thus, the motor driver 29 operates as a switching or digital amplifier to control the operation of the motor 214 and, accordingly, the movement of the scan head 230. The output power from the motor driver 29 allows a portable device, for example, a portable ultrasound system powered by rechargeable batteries, to operate the motor 214 within the volume imaging ultrasound probe 200. Moreover, as the motor 214 slows down, the energy is returned to the motor 214 by the feedback arrangement of the motor driver 29. Accordingly, the energy is not dissipated as heat. Additionally, it should be noted that only one low pass filter 292, 294 is needed at the output of each of the first and second commutators 288, 290, respectively. Typical class D amplifiers need two low pass filters at each output. Thus, the use of large inductors is also reduced, thereby reducing the size requirements for the digital motor driver 29. For example, the digital motor driver 29, in one embodiment, can be implemented in a space of about 70 mm×70 mm×23 mm, resulting in a total area usage of about 112,700 mm$^3$. A typical linear amplifier, on the other hand, uses a space of about 170 mm×110 mm×50 mm, resulting in a total area usage of about 935,000 mm$^3$. Moreover, power consumption using the digital motor driver 29 is, in at least one embodiment, about 3 watts (compared to about 30 watts in a linear amplifier), and a maximum of about 90 watts can be supplied by the battery.

At least one technical effect of the various embodiments of the inventive arrangements is powering and controlling movement of a motor in an ultrasound probe using a portable ultrasound system, including ones using rechargeable batteries.

Some embodiments of the present inventive arrangements provide a machine-readable medium or media having instructions recorded thereon for a processor or computer to operate an imaging apparatus to perform one or more embodiments of the methods described herein. The medium or media may be any type of CD-ROM, DVD, floppy disk, hard disk, optical disk, flash RAM drive, and/or other type of computer-readable medium, and/or any combinations thereof.

The various embodiments and/or components, for example, the processors, or components and controllers therein, may also be implemented as part of one or more computers or processors. Such a computer or processor may include a computing device, an input device, a display unit, and/or an interface, for example, for accessing the Internet. The computer or processor may include a microprocessor. The microprocessor may be connected to a communication bus. The computer or processor may also include a memory. The memory may include Random Access Memory (RAM) and/or Read Only Memory (ROM). The computer or processor may further include a storage device, which may be a hard disk drive or a removable storage drive, such as a floppy disk drive, optical disk drive, and/or the like. The storage device may also be other similar means for loading computer programs and/or other instructions into the computer or processor.

As used herein, the term "computer" may include any processor-based or microprocessor-based system, including systems using microcontrollers, reduced instruction set computers (RISC), application specific integrated circuits (ASICs), logic circuits, and any other circuit or processor capable of executing the functions described herein. The above examples are exemplary only and are thus not intended to limit in any way the definition and/or meaning of the term "computer."

The computer or processor executes a set of instructions that are stored in one or more storage elements, in order to process input data. The storage elements may also store data or other information as desired and/or needed. The storage element may be in the form of an information source or a physical memory element within a processing machine.

The set of instructions may include various commands that instruct the computer or processor as a processing machine to perform specific operations, such as the methods and processes of the various embodiments of the inventive arrangements. The set of instructions may be in the form of a software program. The software may be in various forms, such as system software or application software. In addition, the software may be in the form of a collection of separate programs, a program module within a larger program, or a portion of a program module. The software may also include modular programming in the form of object-oriented programming. The processing of input data by the processing machine may be in response to user commands, or in response to results of previous processing, or in response to a request made by another processing machine.

As used herein, the terms "software" and "firmware" are interchangeable and include any computer program stored in memory for execution by a computer, including RAM memory, ROM memory, EPROM memory, EEPROM memory, and/or non-volatile RAM (NVRAM) memory. The above memory types are exemplary only and thus not limiting as to the types of memory usable for storage of a computer program.

It is to be understood that the above description is intended to be illustrative and not restrictive. For example, the above-described embodiments (and/or aspects thereof) may be used in combination with each other. In addition, many modifications may be made to adapt a particular situation or material to the teachings of the inventive arrangements without departing from their scope. For example, the ordering of steps recited in a method need not be performed in a particular order unless explicitly stated or implicitly required (e.g., one step requires the results or a product of a previous step to be available). While some of the dimensions and types of materials described herein are intended to define the parameters of the inventive arrangements, they are not limiting and are exemplary embodiments. Many other embodiments will be apparent to those of skill in the art upon reviewing and understanding the above description. The scope of the inventive arrangements should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and they are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose the inventive arrangements, including the best mode, and also to enable any person skilled in the art to practice the same, including making and using any devices and/or systems and performing any incorporated methods. The patentable scope of the inventive arrangements is defined by the claims, and it may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. An ultrasound system, comprising:
    a transmitter and receiver, both communicatively coupled to a transducer array of an ultrasound probe, the transducer array driven by a motor having a first coil and a second coil;
    a digital motor driver for controlling movement of the motor to drive the transducer array;
    a first differential amplifier receiving a sine wave control signal and a first feedback signal from the first coil of the motor, wherein the sine wave control signal is compared to the first feedback signal to control a voltage applied to the first coil; and
    a second differential amplifier receiving a cosine wave control signal and a second feedback signal from the second coil of the motor, wherein the cosine wave control signal is compared to the second feedback signal to control a voltage applied to the second coil,
    wherein the motor is driven by the voltages applied to the first coil and the second coil.

2. The ultrasound system of claim 1, wherein the digital motor driver comprises a switch amplifier.

3. The ultrasound system of claim 1, further comprising:
    at least one battery and wherein the digital motor driver is powered by the at least one battery.

4. The ultrasound system of claim 3, wherein the at least one battery comprises a rechargeable battery having an operating voltage of about twelve volts.

5. The ultrasound system of claim 4, wherein the digital motor driver generates an output voltage of about twenty-seven volts from the operating voltage of about twelve volts.

6. The ultrasound system of claim 3, wherein the at least one battery provides a maximum power consumption of about ninety watts.

7. The ultrasound system of claim 1, wherein the digital motor driver is dimensionally sized having a volume of about 112,000 millimeters cubed.

8. The ultrasound system of claim 1, wherein the digital motor driver has a maximum power consumption of about three watts.

9. The ultrasound system of claim 1, wherein the digital motor driver comprises a chopper connected to a pair of commutators.

10. The ultrasound system of claim 9, wherein each of the commutators is connected to one of the first coil or the second coil of the motor of the ultrasound probe.

11. The ultrasound system of claim 9, further comprising:
    a low pass filter connected to an output of each of the commutators.

12. The ultrasound system of claim 11, wherein one of the commutators receives a rectangular input control signal.

13. The ultrasound system of claim 12, wherein a phase of an input control signal is modulated so that an output of the low pass filter is the sine wave control signal.

14. The ultrasound system of claim 12, wherein a phase of an input control signal is modulated so that an output of the low pass filter is the cosine wave control signal.

15. The ultrasound system of claim 1, wherein a speed of the motor is controlled by a frequency of the sine wave control signal and the cosine wave control signal and a direction of the motor is controlled by a phase of the sine wave control signal and the cosine wave control signal.

16. The ultrasound system of claim 1 further comprising at least one digital to analog converter to output one of the sine wave control signal or the cosine wave control signal.

17. The ultrasound system of claim 16 further comprising a second digital to analog converter to output the other of the sine wave control signal and the cosine wave control signal.

18. The ultrasound system of claim 1 further comprising a motor controller electrically coupled to the digital motor driver, the motor controller including programmable logic for generating control signals.

19. A portable ultrasound system, comprising:
    a volume probe having a motor to move a scan head including a transducer array, the motor having a first coil and a second coil;
    a motor controller; and
    a digital motor driver connected to the motor controller and configured to receive control signals from the motor controller to drive the motor of the volume probe to move the scan head;
    a first differential amplifier receiving a sine wave control signal and a first feedback signal from the first coil of the motor, wherein the sine wave control signal is compared to the first feedback signal to control a voltage applied to the first coil; and
    a second differential amplifier receiving a cosine wave control signal and a second feedback signal from the second coil of the motor, wherein the cosine wave control signal is compared to the second feedback signal to control a voltage applied to the second coil,
    wherein the motor is driven by the voltages applied to the first coil and the second coil.

20. The portable ultrasound system of claim 19, further comprising:
    a rechargeable battery that powers the motor controller.

21. The portable ultrasound system of claim 19, wherein the digital motor driver comprises a chopper connected to a first commutator and second commutator.

22. The portable ultrasound system of claim 21, further comprising:
    a low pass filter connected to each of the first and second commutators.

23. The portable ultrasound system of claim 19, wherein a frequency of the sine wave control signal and the cosine wave control signal controls a speed of the motor of the volume probe and a phase of the sine wave control signal and the cosine wave control signal controls a direction of movement of the motor of the volume probe.

24. A method of controlling an ultrasound probe, comprising:
    powering a digital motor driver using a portable power supply to drive a motor of the probe;
    receiving at a first differential amplifier a sine wave control signal and a first feedback signal from a first coil of the motor;
    comparing the sine wave control signal to the first feedback signal to control a voltage applied to the first coil;

receiving at a second differential amplifier a cosine wave control signal and a second feedback signal from a second coil of the motor;

comparing the cosine wave control signal to the second feedback signal to control a voltage applied to the second coil; and controlling movement of a scan head within the probe using the digital motor driver based on the voltages applied to the first coil and the second coil of the motor.

* * * * *